US005601988A

United States Patent [19]
Gordon

[11] Patent Number: 5,601,988
[45] Date of Patent: *Feb. 11, 1997

[54] IMMUNOCAPTURE ASSAY FOR CANCER PROCOAGULANT ANTIBODY COMPLEX IN BIOLOGICAL SAMPLES

[75] Inventor: Stuart G. Gordon, Denver, Colo.

[73] Assignee: ImmunOnc, Inc., Lenexa, Kans.

[*] Notice: The term of this patent shall not extend beyond the expiration date of Pat. No. 4,943,524.

[21] Appl. No.: 246,840

[22] Filed: May 20, 1994

Related U.S. Application Data

[63] Continuation-in-part of Ser. No. 48,421, Apr. 14, 1993, abandoned, which is a continuation-in-part of Ser. No. 135,877, Oct. 13, 1993, abandoned, which is a continuation-in-part of Ser. No. 894,094, Jun. 5, 1992, abandoned, which is a continuation-in-part of Ser. No. 758,524, Sep. 6, 1991, abandoned, which is a continuation-in-part of Ser. No. 247,843, Sep. 22, 1988, abandoned, which is a continuation-in-part of Ser. No. 313,285, Feb. 17, 1989, Pat. No. 4,943,524, which is a continuation of Ser. No. 69,454, Jul. 2, 1987, abandoned.

[51] Int. Cl.$^6$ .................. G01N 33/574; G01N 33/53; G01N 33/537; G01N 33/564
[52] U.S. Cl. .................. 435/7.23; 435/7.92; 435/7.94; 435/975; 436/63; 436/64; 436/507; 436/813
[58] Field of Search .................. 435/7.23, 7.92, 435/7.94, 975; 436/507, 63, 64, 813

[56] References Cited

U.S. PATENT DOCUMENTS

| | | | |
|---|---|---|---|
| 4,711,839 | 12/1987 | Singhal | 435/4 |
| 4,943,524 | 7/1990 | Gordon | 435/7 |

OTHER PUBLICATIONS

Gordon et al. (1978) "Comparison of Procoagulant Activity in Tissue Culture Medium from Normal and Transformed Fibroblasts," *Can. Res.* 38:2467–2472.

Gordon et al. (1979) "Comparison of Procoagulant Activities in Extracts of Normal and Malignant Human Tissue," *J. Natl. Cancer Inst.* 62:773–776.

Donati et al. (1986) "Cancer Procoagulant in Human Tumor Cells:Evidence from Melanoma Patients," *Canc. Res.* 46:6471–6474.

Gordon et al. (1990) "An Enzyme–linked Immunosorbent Assay for Cancer Procoagulant and Its Potential as a New Tumor Marker," *Canc. Res.* 50:6229–6234.

Gordon et al. (1989) "Analysis of Serum Cancer Procoagulant Activity and Its Possible Use as a Tumor Marker," *Thromb. Res.* 56:431–440.

Gordon et al. (1982) "Analysis of Procoagulant Activity of Intact Cells from Tissue Culture," *Thromb. Res.* 26:379–387.

Mielicki et al. (1990) "Cancer Procoagulant in Serum of Rats During Development of Experimental Epithelioma," *Int. J. Cancer* 45:125–126.

Kozwich et al. (1994) "The Clinical Utility of Cancer Procoagulant (CP) as an Early Stage Tumor Marker," ASCO Abstract ASCO Annual Meeting, Dallas, TX, May 14–17, 1994.

*Primary Examiner*—Toni R. Scheiner
*Assistant Examiner*—Yvonne Eyler
*Attorney, Agent, or Firm*—Greenlee, Winner and Sullivan, P.C.

[57] ABSTRACT

This invention provides a specific immunocapture ELISA for the quantitation of cancer procoagulant antibody complex (CPAC) in biological samples. In particular, this invention provides methods and techniques for specifically selecting and quantitatively measuring CPAC from a sample material using anti-CP antibodies followed by labeled anti-immunoglobulin antibodies. The amount of captured CPAC is then determined by measuring the amount of label in the captured CPAC.

18 Claims, 2 Drawing Sheets

IMMUNOCAPTURE ASSAY FOR CANCER PROCOAGULANT ANTIBODY COMPLEX IN BIOLOGICAL SAMPLES

CROSS-REFERENCE TO RELATED APPLICATIONS

This application is a continuation-in-part application of U.S. patent application Ser. No. 08/048,421, filed Apr. 14, 1993 and now abandoned, which is a continuation-in-part application of U.S. patent application Ser. No. 08/135,877, filed Oct. 13, 1993 and now abandoned, which is a continuation-in-part application of U.S. patent application Ser. No. 07/894,094, filed Jun. 5, 1992, abandoned Oct. 28, 1993, which is a continuation-in-part application of U.S. patent application Ser. No. 07/758,524, filed Sep. 6, 1991, abandoned Jul. 23, 1992, which is a continuation-in-part application of U.S. patent application Ser. No. 07/247,843, filed Sep. 22, 1988, abandoned Sep. 6, 1991, which is a continuation-in-part application of U.S. patent application Ser. No. 07/313,285, filed Feb. 17, 1989, issued as U.S. Pat. No. 4,943,524 on Jul. 24, 1990, which is a continuation application of U.S. patent application Ser. No. 07/069,454, filed Jul. 2, 1987, abandoned Feb. 17, 1989.

FIELD OF INVENTION

This invention relates to the quantitation of cancer procoagulant (CP) in biological samples using immunocapture techniques. More particularly, this invention relates to methods and techniques for specifically selecting and isolating CP complexed to an antibody (a CP antibody complex or CPAC) from an aliquot of sample material, followed by the measurement of the amount of antibody bound to CP in the CP antibody complex.

BACKGROUND OF THE INVENTION

Despite many therapeutic advances, early detection of malignancy has great potential as a means of affecting outcome and survival of cancer patients. All too often the disease is too far advanced and therapeutic options are limited. Earlier diagnosis and treatment can affect outcome as evidenced by screening Papanicolou smears for squamous cell carcinoma of the cervix [Lunt (1984) *Obstet. Gynecol.* 63:708–713].

The development of an assay with similar potential for early detection of other malignancies would be of considerable aid to clinical oncologists. Recently, investigators have identified several substances that are produced by tumor cells for use as diagnostic markers of cancer. These include the germ cell markers human choriogonadotropin and α-fetoprotein, which are very specific markers, and less sensitive and specific markers such as carcinoembryonic antigen (CEA), CA-12.5, CA-19.9, CA-15.3, prostate specific antigen (PSA), and others. Recent reviews describe the use of these and other tumor markers in diagnostic and therapeutic applications [Pohl et al. (1983) *Cancer Detect. Prevent.* 6:7–20; Kluvins et al. (1983) *Ann. Clin. Lab. Sci.* 13:275–280; Sultzeanu et al. (1985) *Adv. Cancer Res.* 44:1–42; Virji et al. (1988) *Cancer* 38:105–126; and Sikorska et al. (1988) *Cancer Detect. Prevent.* 12:321–355].

The cysteine protease, cancer procoagulant (CP), E.C. 3.4.22.26, has been isolated and purified [Gordon et al. (1975) *Thrombos. Res.* 6:127–138; Gordon et al. (1981) *J. Clin. Invest.* 67:1665–1671; and Falanga et al. (1985) *Biochemistry* 24:5558–5567] from neoplastic tissue as well as amnion-chorion tissue. It was found that CP activity existed in the extracts of malignant cells, but not in extracts from normal tissue or serum-free media from normal cells in tissue culture [Gordon et al. (1978) *Cancer Res.* 38:2467–2472; Gordon et al. (1979) *J. Natl. Cancer Inst.* 62:773–776; Gordon et al. (1982) *Thrombos. Res.* 26:379–387; and Gordon et al. (1989) *Thrombos. Res.* 56:431–440]. Enzymatic and immunological characterization of extracts of malignant and benign melanocytic tissue revealed CP in the melanoma extracts and not in the benign nevi extracts [Donati et al. (1986) *Cancer Res.* 46:6471–6474]. In acute nonlymphocytic leukemia, CP was identified in most of the cytological subtypes but not in control mononuclear cells from either peripheral blood or bone marrow aspirates [Falanga et al. (1988) *Blood* 71:870–875]. In addition, a virtually identical procoagulant protein has been purified from human amnion-chorion tissue (fetal origin), implying that CP may be an oncofetal protein [Gordon et al. (1985) *Blood* 66:1261–1265; and Falanga et al. (1985) *Biochem. Biophys. Acta* 831:161–165].

Initially, CP was assayed with a one-stage and, later, with a two-stage clotting assays [Gordon et al. (1981) *J. Clin. Invest.* 67:1665–1671; Falanga et al. (1985) *Biochemistry* 24:5558–5567; and Gordon et al. (1985) *Blood* 66:1261–1265]. A direct chromogenic assay for CP was developed by Moore [(1992) *Biochem. Biophys. Res. Com.* 184:819–824]. This assay used the chromogenic substrate, Chromozym TH, which is very specific for thrombin and, therefore, the assay had low specificity and sensitivity. Also, this assay necessitated the use of very pure CP, without traces of coagulation factors or other proteinases.

"Sandwich" enzyme-linked immunosorbent assays (ELISA) are very sensitive and specific because of the high degree of specificity of antibodies for their antigens. An ELISA assay was developed and used to assay CP [Gordon U.S. Pat. No. 4,943,524, issued Jul. 24, 1990, and Gordon et al. (1990a) *Cancer Res.* 50:6229–6234]. CP measurements with ELISA assays in the serum of cancer patients and of noncancerous control individuals led to the characterization of CP as a tumor marker.

In studies described by Gordon et al. (1990b) *Cancer Res.* 50:6229–6234, there was a substantial percentage of false-negative cancer patient sera in both the gastrointestinal and lung cancer groups of patients with late stage cancer. It was noted that several of these "false negative" patients were terminal at the time the blood samples were obtained and that they died from their malignancy shortly thereafter. Blood samples of these cancer patients suggested the presence of endogenous anti-CP antibodies. Evidence was also obtained [Meilicki et al. (1990) *Int. J. Cancer* 45:125–126] for a decreased production of CP activity in the serum of rats with late stage epithelioma, suggesting that CP production in late stage cancers may decrease. Further, it was suggested that in the false negative samples CP may be associated with a serum protein or other substance produced by the tumor that binds CP, blocks the epitope and inhibits the immunoreactivity of CP in the assay.

SUMMARY OF THE INVENTION

The present invention provides a method for the detection and quantitation of cancer procoagulant (CP) that is complexed with an antibody (a CP antibody complex or CPAC) in a biological fluid from a human or an animal. This method for measuring a CP antibody complex comprises the steps of:

(a) exposing an amount of biological sample to an anti-CP antibody in solution phase or adsorbed onto the solid support so that any CP antibody complex in the biological sample is quantitatively captured by the anti-CP antibody;

(b) removing the non-CP material;

(c) exposing the captured CP antibody complex to an anti-immunoglobulin which is conjugated to a label; and (d) determining the amount of label bound to the captured CP antibody complex.

The amount of CP antibody complex in the biological sample is determined from the amount of label bound to the solid support. In preferred embodiments of the invention, the anti-immunoglobulin antibodies (signal antibodies) are conjugated to alkaline phosphatase. p-nitrophenyl phosphate is added as a substrate for the enzyme in order to quantitate the amount of CP antibody complex that is present in the biological sample.

In preferred embodiments of the invention, the amount of CP antibody complex present in cancer patients' sera was measured by:

(a) adsorbing anti-murine CP monoclonal IgM onto a solid support;

(b) exposing an amount of human serum to the IgM bound to the solid support such that the CP antibody complex present in the serum is quantitatively captured by the IgM bound to the solid support;

(c) rinsing away any non-CP material from the solid support;

(d) exposing the captured CP antibody complex to a goat anti-human IgG conjugated to alkaline phosphatase; and (e) exposing the captured CP antibody complex to p-nitrophenyl phosphate to measure alkaline phosphatase activity as a measure of the amount of CP antibody complex present in the serum.

The method of the invention for measuring CP antibody complexes in biological samples contemplates the use of a capture antibody, which can be a monoclonal, polyclonal recombinant or chimeric antibody, and a signal antibody, which can also be a monoclonal, polyclonal recombinant or chimeric antibody. It is preferred that the anti-CP capture antibody be a monoclonal IgM or IgG. It is preferred that the signal anti-immunoglobulin antibody be anti-Ig (anti-immunoglobulins, all subtypes) and, more preferably, that it be an anti-IgG antibody.

In a preferred embodiment of the invention, murine anti-CP monoclonal antibodies, and in particular IgM antibodies, were used to select CP and CP antibody complexed antigens from a biological sample and to bind them specifically. In an alternative embodiment, human monoclonal or recombinant anti-CP monoclonal antibodies are used to capture CP specifically.

With the method of this invention it is possible to detect, capture, and quantify a CP antibody complex in biological samples. This method is specific for CP antigen complexes, easy to use, and is useful at low levels of CP.

Significantly, the method of this invention provides a means for obtaining a measurement of the amount of CP that is complexed with antibody which, when taken together with the measurement of uncomplexed or free CP using standard ELISA assays gives a value for "total" CP (free and CP complexed with antibody). Measurement of both unbound CP and CP complexed with antigen gives a more accurate assessment of the level of CP in a biological sample and in evaluating whether or not the biological sample is malignant. Thus, the invention, by providing a method for obtaining a measurement for CP antibody complexes in biological samples, enables a more exact correlation to be made between cancerous and noncancerous samples, and between different stages in the progression of cancer.

A further aspect of the present invention contemplates the use of the immunocapture assay in distinguishing animals and humans having cancer from those without cancer. The presence of CP has been shown to correlate with the malignant state and is not present in normalcy [Gordon et al. (1990b) supra and Gordon et al. (1979) *J. Natl. Cancer Inst.* 62:773–776]. The method is also useful for monitoring progress of cancer patients undergoing treatment for cancer and for evaluating CP levels in biopsy specimens.

Further, this invention contemplates the preparation of a kit useful for the detection of a CP antibody complex in a biological sample. This kit comprises anti-CP antibodies to quantitatively capture CP antibody complexes present in the sample and anti-immunoglobulin antibodies conjugated with a label to quantify the amount of CP antibody complex.

In a preferred embodiment of this invention, the anti-immunoglobulin antibodies were labeled with alkaline phosphatase and p-nitrophenyl phosphate was added as a substrate; measurement of the enzymatic reaction product gave a direct measure of the amount of CP antibody complex in the biological sample. It is preferred that the detection of CP antibody complex in a sample, using the kit of this invention, correlate directly with the appearance of label or label product. Thus, the kit of the invention is useful in determining whether or not CP is present in a biological sample and, thereby, in detecting the presence of malignancy. Thus, the kit according to the invention has additional utility in screening biological samples for the presence of cancer or in monitoring cancer patients undergoing treatment for cancer.

DETAILED DESCRIPTION OF THE INVENTION

The following definitions are provided in order to provide clarity as to the intent or scope of their usage in the specification and claims.

The term cancer procoagulant (CP) as used herein refers to a proteolytic enzyme that directly activates factor X, bypassing both the extrinsic and intrinsic pathways of the coagulation cascade. CP, isolated from rabbit V2 carcinoma and purified approximately 2,664-fold (Gordon, U.S. Pat. No. 4,461,833), is a 68 kDa protein having an isoelectric point of 4.8. CP is a cysteine proteinase; it is sensitive to cysteine proteinase inhibitors, such as iodoacetamide and mercury, and activators, such as dithiothreitol and KCN; and it binds to p-chloromercuribenzoate agarose [Donati et al. (1986) supra]. CP isolated from human amnion-chorion coprecipitates, comigrates in SDS-PAGE and cross-reacts immunologically with CP isolated from rabbit V2 carcinoma. CP that is chemically modified, for example by addition of chemical or biological ligands or by substitution, addition or deletion of amino acids, is considered to be equivalent to unmodified CP whenever such modifications do not prevent detection of CP enzymatic and immunologic activity in the final product.

The term CP antibody complex or CPAC as used herein refers to CP that is complexed with an antibody in a biological sample.

Ther term total CP as used herein refers to the sum of the free (unbound) CP and the CP complexed to antibody that is present in a biological sample.

The term anti-CP antibodies as used herein refers to either human or animal (e.g., rabbit, mouse, rat, etc.) polyclonal or monoclonal or recombinant or chimeric antibodies developed to purified CP. Methods used to prepare and purify polyclonal, monoclonal, recombinant and chimeric antibodies are known in the art. Anti-CP antibodies used for CP determination are preferably monospecific having an immunoreactivity only to CP.

The term recombinant antibody as used herein refers to a genetically engineered antibody. The amino acid sequence, or partial sequence, of an immunoglobulin is used to probe a hybridoma cell for a corresponding mRNA. The mRNA is then used in PCR techniques using the Invitrogen Corporation PCR cloning systems, e.g., TA Cloning® System, to produce a coding region which enables the production of a desired antibody.

The term chimeric antibody as used herein refers to an antibody expressed by the use of genetic engineering. For example, a DNA sequence from a first organism that codes for an amino acid sequence having a desired specific characteristic or function is inserted into a sequence of DNA of a second organism that codes for an antibody that can be expressed by the use of genetic engineering, so that the DNA sequence that codes for the amino acid sequence having a specific function is connected in a correct position on the recombinant DNA for it to function as an open reading frame. Then plasmids that carry this recombinant DNA are used to transform cells that are capable of producing the antibody. These transformants are cultured by tissue culture or else allowed to replicate in a living organism, so that the chimeric antibody that is to be produced is obtained. A chimeric antibody can comprise a synthetic immunogenic determinant and/or a combination of immunogenic determinants characteristic of different animals, e.g., human/mouse, mouse/rabbit, etc.

The term capture antibody or capture antibodies as used herein refers to anti-CP antibodies which are used to capture (selectively sequester and bind) the CP antibody complex from a biological fluid or a standard solution comprising CP or CP antibody complex.

The term Signal antibody or signal antibodies as used herein refers to anti-immunoglobulin (anti-Ig, all subtypes) antibodies which are conjugated to a label that is readily detectable and measurable.

The term anti-species immunoglobulin antibody as used herein refers to the anti-immunoglobulin antibodies used in the method of the invention wherein the immunoglobulin is derived from the same species of animal as is the antibody in the CP antibody complex.

The terms cancer procoagulant activity or CP procoagulant activity or CP activity as used herein refer to the biological activity of CP in activating coagulation. These terms also refer to the action of CP directly on factor X, converting it to an activated form, factor $X_a$.

The term immunocapture as used herein refers to the selective sequestering and binding of CP antibody complex by anti-CP antibodies adsorbed to a solid support.

The term quantitatively captured as used herein refers to the capture (sequestering and binding) of the CP antibody complex present in an aliquot of a biological or test sample by anti-CP antibodies in solution phase or adsorbed to a solid support. The appropriate amount of biological sample to add to a well of a microtiter plate comprising anti-CP antibodies is predetermined by assaying various dilutions of the biological sample.

The term a label as used herein refers to the labeling of a molecule using any of a variety of labels and methods of labeling known in the art. Examples of types of labels encompassed by the present invention include, but are not limited to, radioisotopic labels (e.g., $^{125}I$, $^{131}I$, $^{35}S$, $^{14}C$, etc.), non-radioactive isotopic labels $^{55}Mn$, $^{56}Fe$, etc.), fluorescent labels (e.g., a fluorescein label, an isothiocyanate label, a rhodamine label, a phycoerythrin label, a phycocyanin label, an allophycocyanin label, an o-phthaldehyde label, a fluorescamine label, etc.), chemiluminescent labels, enzyme labels (e.g., alkaline phosphatase, horse radish peroxidase, etc.), protein labels, etc.

The term biological sample as used herein refers to body fluids, for example, plasma, serum, saliva, urine, lung lavage fluid, cyst fluid, etc., from a mammal, such as humans, primates, rodents (i.e., mice, rats, rabbits), bovines, ovines or canines. This term also encompasses tissue extracts wherein the tissue pieces are removed and separated from the liquid extract.

The presence of CP is associated with the malignant state and is not found to correlate with normalcy [Gordon et al. (1989) *Thromb. Res.* 56:131–140]. Therefore, CP, as a tumor marker, can be used to detect malignancy. Gordon et al. (1990b) supra reported the ability to distinguish normal sera from sera of cancer patients by measuring the presence of CP in the sera. The percentage of false positive results for the normal sera was within the limits of the expected value. There appeared to be a problem, however, in that a substantial percentage of false negative results were obtained in cancer patient sera in groups of patients with late stage cancer.

This problem is remedied by the method of the instant invention. The present invention discloses the discovery that CP in sera of cancer patients is not all in the free form but also is complexed with antibody. Thus, the inability to measure the CP that is complexed with antibody (CP antibody complex) underestimates the amount of CP in biological samples and can lead to false negative results. The present invention, which is a method for measuring CP antibody complexes in a biological sample, enables the computation of the total amount of CP (free and complexed forms of CP) in samples of cancer patients and allows identification of CP levels indicative of malignancy.

The method of the present invention is a double antibody ELISA assay developed specifically for assaying CP antibody complexes in patient samples. The ELISA method of the present invention differs from standard ELISA assays known in the art. [see *Antibodies, A Laboratory Manual* (Harlow, E. and Lane, D. eds.) 1988, Cold Spring Harbor Laboratory, Cold Spring Harbor, N.Y.] Standard ELISA assays require two antibodies that bind to nonoverlapping epitopes on the same antigen and routinely utilize either two monoclonal antibodies that recognize discrete sites on an antigen or one batch of affinity-purified polyclonal antibodies. The ELISA method of the instant invention utilizes two antibodies, each of which recognizes a different antigen, i.e., an anti-CP antibody and an anti-immunoglobulin antibody.

In the present method, antibodies specific to CP are utilized first to specifically select and capture CP antibody complexes from a biological sample. Then, antibodies specific to immunoglobulin are used to specifically target the antibody in the CP antibody complex. Under standard art known ELISA assay conditions, only anti-CP antibodies are used and, therefore, only free CP is measured and any CP that is complexed with antibody remains undetected. In contrast, the method of the instant invention requires and ensures the detection not only of the CP component but also of the immunoglobulin component in the CP antibody complex and, thereby, enables a reliable measurement to be made of the amount of CP antibody complex present in a biological sample. Once the amount of CP complexed to antibody in a sample is known, it is then possible to obtain an accurate measure of the total amount of CP (free and complexed to antibody) in the sample. This invention prevents the underestimation of CP in biological samples and thereby prevents or reduces the occurrence of false negative results.

Figure 1:
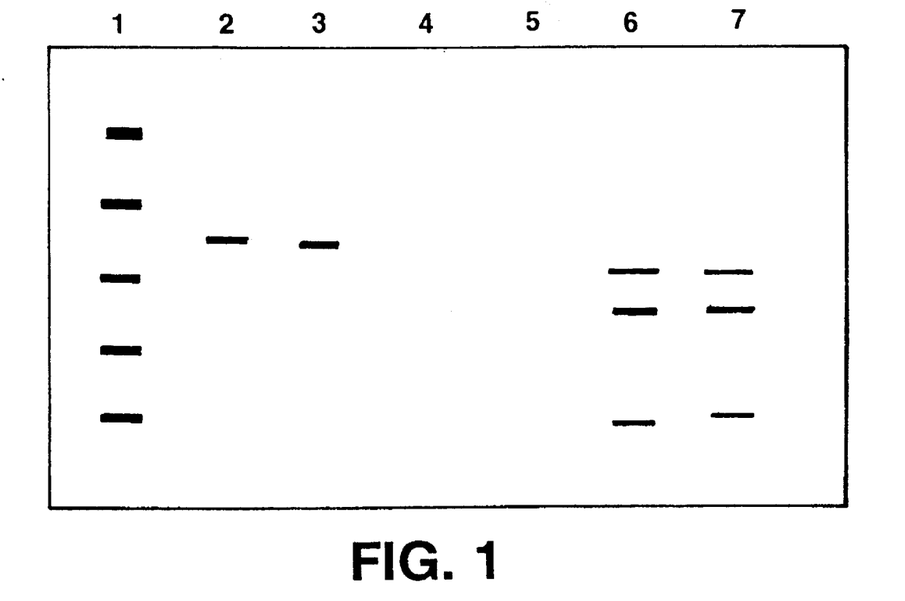
FIG. 1 presents silver stained SDS-PAGE gel of elutates from IgM MAb coated microtiter plates. Samples were added to microtiter plates coated with anti-CP IgM MAb. After incubation and washing, the 50% ethylene glycol eluate was aspirated and pooled; the protein was TCA precipitated and analyzed by SDS-PAGE on a 10% polyacrylamide gel Lane 1= molecular weight standards: 200, 000, 97,400, 68,000, 46,000 and 30,000 daltons; Lane 2= eluate from the de-adsorption of IgM MAb; Lane 3= blocking reagent only; Lane 4= false positive serum sample; Lane 5= true negative serum sample; Lane 6= true positive serum sample and Lane 7= false negative serum sample.

In FIG. 1 are shown the results of analyzing true positive, true negative, false positive and false negative serum samples by eluting from immobilized anti-CP MAb with 50% ethylene glycol. The eluate was TCA precipitated and the protein was separated by SDS-PAGE on a 10% polyacrylamide gel. CP has a molecular weight of 68,000 daltons, the molecular weight of heavy chain polypeptides are 55,000 daltons and the molecular weight of the light chain polypeptides are 25,000 daltons. The presence of CP and the heavy and light chains of immunoglobulin in the true positive and the false negative samples, lanes 6 and 7 respectively, are indicated by the bands at 68, 55, and 25 Kd. The false positive and true negative serum samples, Lanes 4 and 5 respectively, do not have bands corresponding to CP and heavy and light chains of immunoglobulins.

Figure 2:
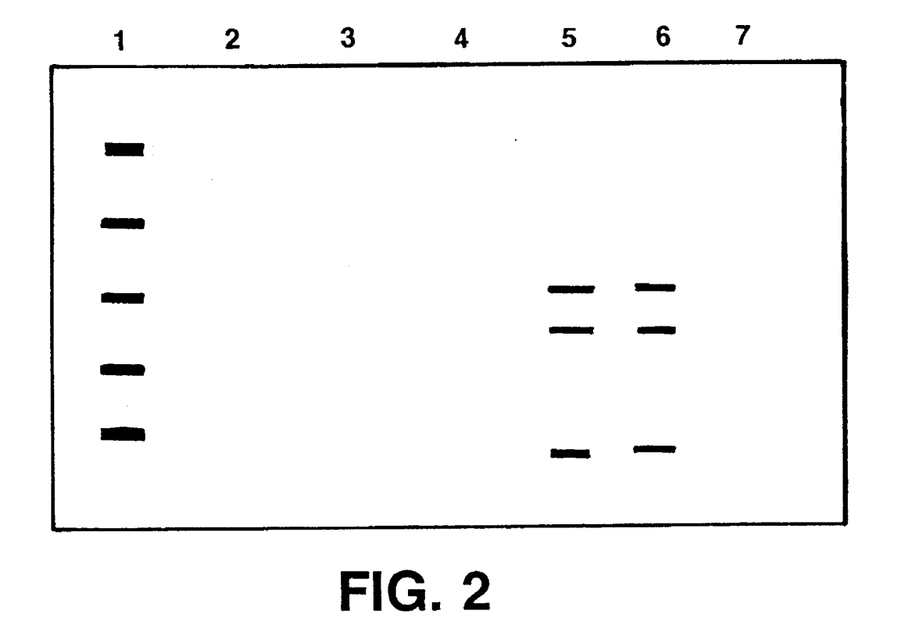
FIG. 2 presents immunoblotting of eluates from IgM MAb coated microtiter plates. Samples were added to microtiter plates coated with anti-CP IgM MAb. After incubation and washing, the eluate was aspirated and pooled, the protein was TCA precipitated and separated by SDS-PAGE. Separated proteins were transferred to nitrocellulose and immunoblotted with goat anti-CP antibody and goat anti-human IgG. The signal antibody was rabbit anti-goat alkaline phosphatase labeled conjugate. Lane 1= molecular weight standards: 200,000, 97,400, 68,000, 46,000 and 30,000 daltons; Lane 2= eluate from the de-adsorption of IgM MAb; Lane 3= blocking reagent only; Lane 4= false positive serum sample; Lane 5= true positive serum sample; Lane 6= false negative serum sample and Lane 7= true negative serum sample.

That the bands represent CP and immunoglobulin heavy and light chains is confirmed in the immunoblots blots shown in FIG. 2. The CP was probed with goat anti-CP polyclonal antibody, followed by alkaline phosphatase labeled anti-goat IgG as the secondary antibody. The immunoglobulin was probed with goat anti-human IgA, IgM and IgG antibody labeled with alkaline phosphatase. The bands in lanes 5 and 6 indicate that CP and human immunoglobulins are present in the samples eluted from the anti-CP MAb coated plates.

Figure 3:
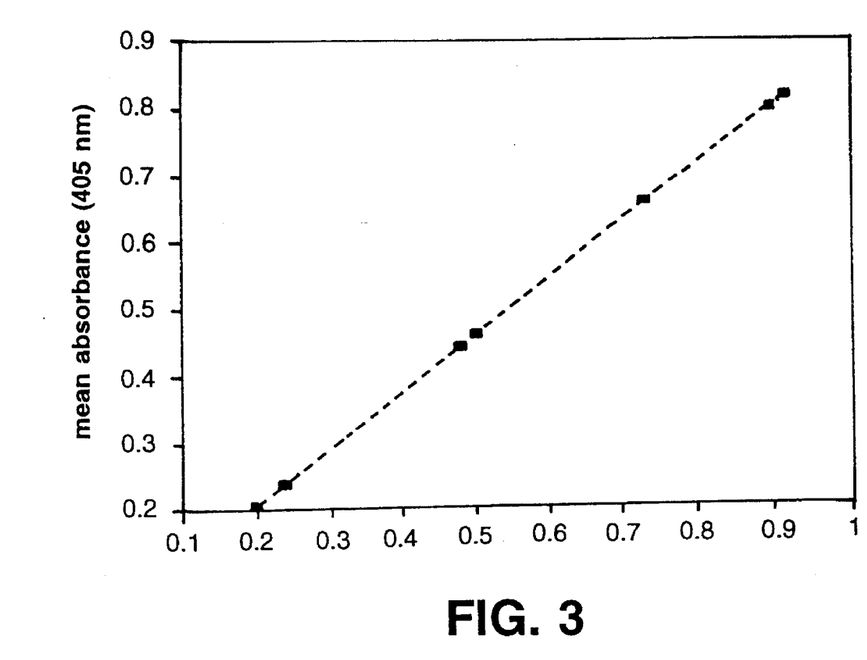
FIG. 3 presents a standard curve of an IgG standard (top) and for an IgG-CP complex (bottom).

The results of calibration of the IgG-CP complex standard curve is shown in FIG. 3. The standard curve constructed from adsorbing known concentrations of IgG onto microtiter plate wells is shown in FIG. 3 (top). Regression analysis of four separate trial is indicated as well as the 95% confidence interval. The concentration of the IgG-CP complex was determined from this curve and is illustrated in FIG. 3 (bottom).

The results of analyzing 162 individuals, 108 cancer sera and 54 noncancer sera are shown in Table 1.

TABLE 1

|  | CP ELISA | | CP ANTIBODY COMPLEX ELISA | | |
|---|---|---|---|---|---|
|  | + | − | + | − | TOTAL |
| Cancer Population | 78 | 30 | 92 | 16 | 108 |
| Noncancer Population | 9 | 45 | 9 | 45 | 54 |
| Sensitivity | 72.2% | | 85.2% | | |
| Specificity | 83.3% | | 83.3% | | |

+ = ELISA positive;
− = ELISA negative

The CP ELISA (art known ELISA assay using standard protocol to measure free CP) was able to detect 78 out of 108 samples correctly. The sensitivity of the assay was 72.2%. When the results from the ELISA assay of the present invention, which detects CP-immune complexes, were added to the CP ELISA results, the data improved by 13%. The ELISA assay of the present invention was able to correctly identify 92 cancer sera samples out of 108 patients. The sensitivity improved to 85.2%. There was not any change in the specificity of the assay.

An analysis of the number of positive and negative sera samples for the cancer and noncancer population, as well as the sites of cancer for the cancer population is illustrated in Table 2.

TABLE 2

| CANCER POPULATION | | | | |
|---|---|---|---|---|
|  | POS | NEG | N | SEN |
| (a) With the Standard CP ELISA Assay | | | | |
| Colon | 6 | 2 | 8 | 75% |
| Breast | 12 | 3 | 15 | 80% |
| Prostate | 6 | 3 | 9 | 66% |
| Lung | 17 | 6 | 23 | 73.9% |
| Other Cancers | 37 | 16 | 53 | 69% |
| Total Number | 78 | 30 | 108 | 73.2% |
| (b) With the Additional ELISA Assay for CP Antibody Complex | | | | |
| Colon | 6 | 2 | 8 | 75% |
| Breast | 13 | 2 | 15 | 86.7% |
| Prostate | 6 | 3 | 9 | 66% |
| Lung | 23 | 0 | 23 | 100% |
| Other Cancers | 44 | 9 | 53 | 83% |
| Total Number | 92 | 16 | 108 | 85.2% |

The sensitivity of breast cancer was increased to 86.7%. Lung cancer was correctly diagnosed 100% with the CP antibody complex assay, an increase in sensitivity of 26.1%. "Other" cancers also improved by 13.2%. Other cancers include ovarian, melanoma, pancreatic, head and neck cancers, lymphoma and leukemia. The ELISA CP antibody complex assay did not improve the sensitivity of colon or prostate cancers in this set of serum samples.

The analysis for the inter- and intra-assay precision is illustrated in Table 3.

TABLE 3

| Pool | N | Mean (µg IgG-CP/ml) | Standard Deviation | % CV |
|---|---|---|---|---|
| Intra-assay precision | | | | |
| A | 8 | 0.2 | 0.009 | 4.6 |
| B | 8 | 1.0 | 0.021 | 2.1 |
| C | 8 | 1.7 | 0.077 | 4.6 |
| Inter-assay precision | | | | |
| A | 18 | 0.39 | 0.057 | 14.6 |
| B | 18 | 1.05 | 0.037 | 3.6 |
| C | 18 | 1.66 | 0.054 | 3.2 |

The intra-assay precision was 4.6% coefficient of variation (CV) for the low CP-IgG complex sample with a mean concentration of 0.205 µg/ml and a standard deviation of 0.009. The precision for the medium CP-IgG complex sample was 2.1% CV with a mean concentration of 1.0 µg/ml and a standard deviation of 0.021. The sample containing the highest concentration of CP-IgG complex had a %CV of 4.6 with a mean concentration of 1.665 µg/ml and a standard deviation of 0.077.

The inter-assay precision was determined for three samples. The lowest concentration of the IgG-CP complex had the highest inter-assay %CV, 14.6. The mean concentration was 0.39 µg/ml and a standard deviation of 0.057. The inter-assay precision of the medium and high levels of the complex had excellent precision with %CVs of 3.6% and 3.2%, respectively.

In this method, the CP antibody complex present in a biological sample, for example, plasma, serum, saliva, urine, lung lavage fluid, cyst fluid, tissue extract, etc., is selectively captured from the sample by anti-CP antibodies. The immunocapture assay can be performed in solution phase or on solid support as is well known in the art. In a preferred embodiment of the invention, the anti-CP antibodies are affixed onto a solid support by any stable interaction known to the art such as hydrophobic, electrostatic or covalent interaction. Some examples of solid supports are microtiter plates, magnetic particles, beads, sheets, membranes, chromatography resins, e.g., Sepharose, etc. Preferably, multi-well microtiter plates or nitrocellulose membranes are used, so that when the CP antibody complex antigen is captured by anti-CP antibodies, the resultant immunological complex is immobilized and easily isolated, e.g., by rinsing away non-CP material remaining in the biological sample. Further, it is preferred that monoclonal anti-CP antigens be utilized preferentially as the capture antibodies in this invention. Also, it is preferred that monoclonal or affinity-purified polyclonal anti-immunoglobulin and, preferably, that anti-human IgA or IgM and, more preferably, that anti-human IgG be utilized in the invention. The use of human, murine, recombinant, or chimeric monoclonal antibodies is preferentially contemplated by this invention.

In a specific embodiment of the invention the anti-immunoglobulin antibody (signal antibody) is conjugated to alkaline phosphatase, the activity of which, in the presence of substrate, i.e., p-nitrophenyl phosphate, is determined spectrophotometrically at 405nm and is a direct measure of the amount of CP antibody complex in a biological sample. Other labels may be conjugated to the signal antibody, particularly with the aim of enhancing sensitivity of the assay. For example, an anti-human immunoglobulin antibody can be utilized that contains a label known to the art that is easily measured, for example, a radioisotope or a useful chemical group, such as biotin, a chromophore, a fluorophore, or a hapten which could bind to an antibody, or an enzyme. The label or labeled product may be measured, as known to the art, directly or may be separated from the labeled precursors on the basis of solubility, charge or size.

The method of this invention has utility in screening biological samples to detect malignancy through the measurement of high levels of CP procoagulant activity in the sample material. This invention also contemplates the preparation of a kit useful for the detection of CP in a biological sample. Such a kit comprises in close confinement anti-CP antibodies, capable of binding CP antibody complexes, adsorbed onto a solid support, preferably a microtiter plate having from approximately four to approximately ninety-six wells and, more preferably, a nitrocellulose membrane strip; anti-immunoglobulin antibodies, preferably anti-human IgG antibodies, conjugated to a label; and, where necessary, a means for measuring said label, e.g., the presence of p-nitrophenyl phosphate as a substrate for alkaline phosphatase activity.

The appearance of signal from one label in the microtiter well or on the nitrocellulose membrane strip signifies the presence of CP antibody complexes in the biological sample. In a preferred embodiment of such a kit, a nitrocellulose membrane strip comprising anti-CP antibodies is dipped sequentially into the various solutions comprising CP labeled anti-immunoglobulin antibodies, and substrates necessary for the detection of label. The appearance of label (e.g., color) on the nitrocellulose membrane strip signals the presence of CP in the assayed biological sample.

In a specific embodiment of the instant invention the kit comprises anti-CP antibodies, anti-immunoglobulin antibodies labeled with enzyme, and substrate molecules. The biological activities of these proteins are stabilized and preserved at room temperature by lyophilization and/or the addition of a stabilizing agent, e.g., sugar, preferably disaccharide, to each protein suspended in a buffered solution followed by desiccation. Before use, each protein is restored to a biologically active configuration through the addition of water to the lyophilization.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to achieve the method of CP measurement described herein and how to employ those alternatives to achieve functional equivalents of the method of the present invention. It is intended that the present invention include those variants, modifications, alternatives, and equivalents which are appreciated by the skilled artisan and encompassed by the spirit and scope of the present disclosure.

It is understood in the art that modifications may be made to the reaction conditions and specific elements used in the immunocapture enzyme assay to enhance the sensitivity of the assay to measure CP. For example, it is contemplated that a substitution may be made in the choice of the chromogenic substrate or that a ligand (e.g., chemical group) may be added to the signal antibody without affecting the specificity of the assay of this invention. It will also be understood that optimization of CP antibody complex determination encompasses art-known alterations and modifications of reagents and conditions of the method of invention, as will be apparent to those skilled in the art using the teachings of this disclosure.

The following examples are provided for illustrative purposes only and are not intended to limit the scope of the invention.

EXAMPLE 1

Material and Methods (a) Preparation of Reagents

Monoclonal anti-CP antibody IgM (MAb) was prepared, characterized and verified for quality control according to methods described previously Gordon et al. (1990b) supra. The secondary antibody, affinity purified goat antibody to human IgA, IgM and IgG conjugated to alkaline phosphatase was purchased from Kirkegaard and Perry Laboratories, Gaithersburg, Md. Standards were calibrated against goat IgG purchased from Sigma Chemical Co., St. Louis, Mo. Conjugate and secondary antibody was diluted in conjugate diluent buffer [50 mM Tris buffer (pH 7.2)], containing 150 mM NaCl, 1 mM $MgCl_2$, 1 mM $ZnCl_2$, 0.1% sucrose, 0.001% bovine serum albumin (BSA) and 0.01% $NaN_3$.

(b) Preparation of Standards.

The standards were prepared from a pool of cancer patient sera which had high absorbance in the CPAC ELISA. The serum was serially diluted with 20 mM Tris buffer (pH 7.4) containing 10% human serum albumin (Baxter Healthcare Corp., Glendale, Calif.). The serum pool was then calibrated against commercially available human IgG. Briefly, the human IgG was pretreated in 100 mM glycine buffer (pH 2.5) at 1:10 dilution for 10 minutes at 22° C. prior to further dilution in 100 mM potassium phosphate buffer (pH 8.0) containing 0.1% M NaCl to obtain 1.0, 0.5, 0.25, 0.125, 0.063 and 0.032 µg/ml concentrations of IgG. The 100 µl of diluted IgG was adsorbed onto ELISA strip wells (1×8 strips, Corning Glass Works, Corning, N.Y.) for 15 hours at 4° C. The IgG was aspirated and washed 4 times (EL 403 E Microplate Autowasher, Bio-Tek Instruments, Winooski, Vt.) with 20 mM Tris buffer (pH 7.4) containing 150 mM NaCl and 0.05% Tween-20 (TBS-T). The wells were blocked with Superblock (Pierce Chem. Co., Rockford, Ill.) as described by the manufacturer and set aside until the serum pool had been captured by anti-CP MAb adsorbed onto microtiter strips. Briefly, 100 µl of anti-CP MAb was adsorbed onto microtiter plates (1×8 strips, Corning Glass Works, Corning, N.Y.) overnight at a concentration of 1 µg/ml MAb for 15 hours at 4° C. and blocked as described above. 100 µl of each dilution of the serum pool was added in triplicate to the MAb coated wells. The CP-IgG complex was captured from the diluted serum pool by the MAb during a 2 hour incubation at 37° C. The sera was removed from the wells by aspiration and the wells were washed 4 times with the wash buffer described above. At this point, the IgG coated strips were added to the frame containing strips of captured CP-IgG complex and the assay was finished as a single 96 well microtiter plate. The anti-human alkaline phosphatase conjugate was diluted 1:1000 in conjugate diluent buffer, 100 µl of the conjugate was added to the plate and incubated for 1 hour at 37° C. The secondary antibody was removed by aspiration and washed 4 times with TBS-T. p-nitrophenyl phosphate substrate was added (100 µl) to each of the wells and incubated at 22° C. for 1 hour prior to adding 100 µl of 1M NaOH as stopping reagent. The absorbance was read on a microtiter plate spectrophotometer (UV Max Microtiter Plate Reader, Molecular Devices, Menlo Park, Calif.) at a wavelength of 405 nm. A standard curve was constructed from the signal generated by the IgG adsorbed onto the wells. The CP-IgG complex signal was treated as an unknown and the concentration of the complex was determined from the standard curve.

EXAMPLE 2

Elisa Assay for the Determination of CP Antibody Complex

The capture antibody, IgM MAb, was adsorbed onto ELISA wells in microtiter plates (1×8 strips, Corning Glass Works Corning, N.Y.) for 15 hours at 4° C., aspirated and washed 4 times with TBS-T. The wells were blocked with Superblock as described by the manufacturer. Standard, patient and control sera were added (50 µl/well) to the IgM MAb coated wells in triplicate (Biomek 1000 Automated Laboratory Workstation, Beckman Instruments, Fullerton, Calif.). The plates were sealed with tape and incubated for 2 hours at 37° C. in a humid chamber. The serum was removed from the wells by aspiration and the wells were washed as described above. Secondary antibody was diluted (1:1000) in conjugated diluent buffer [50 mM Tris buffer (pH 7.2)] containing 150 mM NaCl, 1 mM $MgCl_2$, 1 mM $ZnCl_2$, 0.1% sucrose, 0.001% bovine serum albumin (BSA) and 0.01% $NaN_3$. The diluted conjugate was added to wells (50 µl/well) and incubated for 1 hour at 37° C. Conjugate solution was removed by aspiration and the wells were washed 8 times with TBS-T. The substrate, p-nitrophenyl phosphate, was added to the wells (50 µl/well) and incubated for 1 hour at 22° C. before adding an equal volume of 1M NaOH as stopping reagent. The absorbance was read on a microplate spectrophotometer (UV Max Microtiter Plate Reader, Molecular Devices, Menlo Park, Calif.) at a wavelength of 405 nm.

EXAMPLE 3

Elution of CP-IgG Complexes from IgM Coated Plates

Sera were characterized as true positive, false positive, true negative, and false negative based on the physician's diagnosis and the results of the CP antibody complex ELISA assay. Each of these sera was incubated for 2 hours on an entire plate (100 µl/well) coated with anti-CP MAb at 37° C. in a humid chamber. The sera were removed by aspiration and washed as described above. 100 µl of a 50% ethylene glycol/phosphate buffered saline [100 mM phosphate (pH 7.4) containing 0.15M NaCl] solution was incubated at 37° C. for 1 hour. The resulting eluate was collected from each plate. The samples were precipitated with trichloroacetic acid (TCA) and analyzed by SDS-polyacrylamide gel electrophoresis (SDS-PAGE) using a Mini-Protean II Dual Slab Cell (BioRad Laboratories, Richmond, Calif.).

EXAMPLE 4

Western and Immunoblotting

Sera from true positive, false positive, true negative and false negative individuals were eluted from IgM coated plates as described above. The proteins from the TCA precipitated samples were separated by SDS-PAGE. The proteins were transferred to nitrocellulose using a Mini Trans-Blot Electophoretic Transfer Cell (BioRad Laboratories, Richmond, Calif.). The nitrocellulose was blocked with 10% nonfat dried milk in TBS overnight at 4° C. Alkaline phosphatase labeled antibody to human IgA, IgM and IgG was diluted 1:1000 in 1% nonfat dried milk dissolved in TBS containing 0.1% Tween for 2 hours at 22° C. The nitrocellulose was washed with TBS-Tween and developed in p-nitrophenyl to the desired intensity.

EXAMPLE 5

Analysis of Human Serum Sample

The serum samples were collected at the University of Colorado Health Sciences Center (Denver, Colo.), Boston Biomedica, Inc. (West Bridgewater, Mass.) and Ciba Corning Diagnostics (Alameda, Calif.). Informed consent was obtained from each of the donors. The samples consisted of a mix of benign, normal and cancer sera. The serum was stored at −70° C. until used in the assay.

EXAMPLE 6

Precision Studies

Intra-assay precision was determined by examining three concentration of samples in the CP antibody complex ELISA assay. Each sample was analyzed eight times and the concentrations were determined from a single standard curve.

Inter-assay precision was determined by examining three samples in six separate CP antibody complex ELISA determinations. The samples were run in triplicate, and the mean of the triplicate value was used to determine the concentration of the sample from each separate standard curve.

EXAMPLE 7

Detection of CP Antibody Complex in Biological Sample Using a Kit

A kit useful for the detection of CP in biological samples comprises anti-CP IgM antibodies, capable of binding CP antibody complexes, adsorbed onto a microtiter plate; anti-immunoglobulin antibodies conjugated to an alkaline phosphatase label; p-nitrophenyl phosphate; and diluents comprising buffer solutions, e.g., phosphate, Tris, etc., salts, etc. These protein, substrate, and buffer solutions are prepared essentially as described in Example 2, except that the concentration of each solution is adjusted so that approximately a drop of each solution will deliver the required amount of reagent for the CP assay.

An aliquot (preferably, one or two drops) of a biological sample (preferably, serum or saliva) or a buffer control is added to a microtiter well containing adsorbed anti-CP antibodies and incubated to allow antigen to become adsorbed, e.g., at 37° C. for one to two hours, at room temperature overnight, etc. After rinsing three times with TBS (20 mM Tris buffer with 0.15M NaCl, pH 7.4), containing 0.05% Tween-20, the captured CP antibody complex is exposed to anti-human IgG antibodies labeled with alkaline phosphatase at 37° C. for one hour, then to a drop of p-nitrophenyl phosphate solution for approximately sixty minutes at room temperature. Washes with buffer solutions are performed when necessary and diluents comprising buffer solutions may be added to adjust concentrations of reactants. In biological samples possessing CP, a colored product is produced. Samples devoid of CP do not produce a colored product.

I claim:

1. A method for measuring cancer procoagulant (CP) that is complexed with an antibody (a CP antibody complex) in a biological sample of an animal species comprising the steps of:

(a) adsorbing an anti-CP antibody onto a solid support;

(b) contacting an amount of said biological sample to said anti-CP antibody adsorbed onto said support so that said CP antibody complex is quantitatively captured by said anti-CP antibody adsorbed onto said solid support;

(c) rinsing away the non-CP material from said solid support;

(d) contacting said captured CP antibody complex to an anti-immunoglobulin antibody conjugated to a label, wherein said immunoglobulin is of said species; and (e) determining the amount of said label bound to said solid support.

2. The method of claim 1 wherein said animal species is a human.

3. The method of claim 1 wherein said biological sample is serum.

4. The method of claim 1 wherein said anti-CP antibody is a monoclonal antibody.

5. The method of claim 4 wherein said monoclonal antibody is an IgM antibody.

6. The method of claim 1 wherein said anti-immunoglobulin antibody is an anti-human immunoglobulin antibody.

7. The method of claim 6 wherein said anti-human immunoglobulin antibody is selected from the group consisting of an anti-human IgA antibody, an anti-human IgG antibody and an anti-human IgM antibody.

8. The method of claim 7 wherein said anti-human immunoglobulin antibody is an anti-human IgG antibody.

9. The method of claim 1 wherein said label is selected from the group consisting of a radioisotope, a biotin, a chromophore, a fluorophore, a chemiluminescent moiety, a hapten and an enzyme.

10. The method of claim 9 wherein said label is an enzyme.

11. The method of claim 10 wherein said label is alkaline phosphatase.

12. A kit useful for the measurement of cancer procoagulant (CP) that is complexed with an antibody (a CP antibody complex) in a biological sample of an animal species and/or for the detection of cancer in a patient having a tumor which produces or is associated with cancer procoagulant (CP) by detecting a CP antibody complex in a biological sample comprising:

an anti-CP antibody, which binds a CP antibody complex, absorbed onto a solid support; and an anti-immunoglobulin antibody conjugated to a label, wherein said immunoglobulin is of said species.

13. The kit of claim 12 wherein said animal species is a human.

14. The kit of claim 12 wherein said anti-CP antibody is a monoclonal antibody.

15. The kit of claim 12 wherein said anti-immunoglobulin antibody is an anti-human immunoglobulin antibody.

16. The kit of claim 15 wherein said anti-human immunoglobulin antibody is selected from the group consisting of an anti-human IgA antibody, an anti-human IgG antibody and an anti-human IgM antibody.

17. The kit of claim 12 wherein said label is selected from the group consisting of a radioisotope, a biotin, a chromophore, a fluorophore, a chemiluminescent moiety, a hapten and an enzyme.

18. A method for the detection of cancer in a patient having a tumor which produces or is associated with cancer procoagulant (CP) comprising the method of measuring a CP antibody complex in a biological sample comprising the steps of:

(a) obtaining from said patient said biological sample selected from the group consisting of a biological fluid and a tissue extract;

(b) contacting an amount of said biological sample to an anti-CP antibody adsorbed onto a solid support so that said CP antibody complex in said biological sample is quantitatively captured by said anti-CP antibody adsorbed onto said solid support;

(c) rinsing away the non-CP material from said solid support;

(d) contacting said captured CP antibody complex to an anti-immunoglobulin antibody conjugated to a label, wherein said immunoglobulin is of said species;

(e) determining the amount of said label bound to said solid support; and (f) whereby a condition of cancer is indicated for said patient exhibiting in step (e) a level of CP antibody complex in said biological sample that is over and above the background or control normal level.

* * * * *